United States Patent [19]
Kurz

[11] Patent Number: 5,857,849
[45] Date of Patent: Jan. 12, 1999

[54] SELF-LIGATING LOW PROFILE ORTHODONTIC BRACKET

[76] Inventor: Craven Kurz, 4267 Marina City Dr., #714, Marina del Ray, Calif. 90292

[21] Appl. No.: 760,455

[22] Filed: Dec. 6, 1996

[51] Int. Cl.⁶ .................................................. A61C 3/00
[52] U.S. Cl. ............................................. 433/10; 433/11
[58] Field of Search ............................... 433/8, 9, 10, 11, 433/12, 13, 14, 15, 16

[56] References Cited

U.S. PATENT DOCUMENTS

| | | | |
|---|---|---|---|
| 3,043,006 | 7/1962 | Wallshein | 433/11 |
| 3,218,715 | 11/1965 | Wallshein | 433/8 |
| 3,964,165 | 6/1976 | Stahl | 433/8 |
| 4,103,423 | 8/1978 | Kessel | 433/10 |
| 4,337,037 | 6/1982 | Kurz | 433/8 |
| 4,547,153 | 10/1985 | Taylor | 433/8 |
| 4,698,017 | 10/1987 | Hanson | 433/11 |
| 4,712,999 | 12/1987 | Rosenberg | 433/8 |
| 4,927,360 | 5/1990 | Pospisil | 433/8 |
| 5,474,445 | 12/1995 | Voudouris | 433/10 |

*Primary Examiner*—John J. Wilson
*Attorney, Agent, or Firm*—Terrell P. Lewis; Keith D. Beecher

[57] ABSTRACT

A low profile self-ligating orthodontic bracket having a base plate which may be adhesively attached to the lingual or labial surface of a tooth, and which includes a transverse slot extending across the front surface of the base plate for receiving an arch wire, and which includes a cover plate extending over the slot and resiliently self-biased against the front surface of the base to force the arch wire down into the slot. The cover plate may be turned outwardly by the orthodontist to permit the arch wire to be inserted into the slot or removed from the slot, and when the cover plate is released, it moves with force against the front surface of the base to trap the arch wire in the slot.

9 Claims, 12 Drawing Sheets

SELF-LIGATING LOW PROFILE ORTHODONTIC BRACKET

BACKGROUND OF THE INVENTION

The invention is concerned with an improved low profile self-ligating orthodontic bracket which may be adhesively attached to the lingual or labial surface of a tooth.

Self-ligating orthodontic brackets are known and are described, for example, in Wallshein Patents 3,052,028 and 3,724,074 as well as in other patents. Rosenberg Patent 4,712,999, for example, discloses a convertible self-ligating orthodontic bracket which is effective, but which involves a separate cover plate rotatable attached to the bracket base. The Rosenberg appliance makes no provision for arch wires that don't get fully engaged into the arch wire slot. A feature of the self-ligating orthodontic bracket of the present invention is its simplicity in that it involves a unitary integral construction without separate parts which are susceptible to being accidentally swallowed and which are difficult to apply. Also, if an arch wire is not fully engaged into the arch wire slot, the feature of this self-ligating bracket is that the continuous pressure applied by the bracket cover continually, progressively pulls the arch wire into the arch wire slot so the arch wire may exert its force when tightly engaged. This makes this simple self-ligating bracket active in part while the other action necessary for tooth positioning is the arch wire force itself.

As pointed out in the Rosenberg patent, there has been a steady improvement in orthodontic devices, and the trend has been to miniaturization and enhanced appearance from a cosmetic viewpoint, as well as increased simplification in the installation and removal procedures. At present, small slotted brackets are employed which are bonded directly to the labial or lingual surfaces of the teeth. A curved arch wire conforming to the patient's dental arch is formed of a special alloy, and pre-torqued by the orthodontist to produce the desired movement of the patient's teeth. This arch wire is fitted into the slots in the brackets in accordance with the prior art practice and the arch wire is tied down to each bracket by a arch wire or elastic donut. The application of the ligating wire requires considerable skill on the part of the orthodontist and long chair time for the patient. Moreover, the arch wire often must be removed from time to time for bending or replacement during the course of the treatment, calling for repetitive ligating operations and increased patient/orthodontist time.

When elastic donuts are used, they have a tendency to discolor and, in addition, they rapidly lose their elasticity. Accordingly, the efficiency of elastic donuts in securing the arch wire to the base of the bracket diminishes and they quickly become ineffective.

These foregoing disadvantages point to the desirability for each orthodontic bracket to incorporate a rapid clamping and unclamping device, that is, to be self-ligating, so that the need for ligating wires, elastic donuts and the like may be reduced, if not completely eliminated.

As mentioned above, prior self-ligating brackets conceived to overcome the foregoing problems have usually resulted in complex structures which are expensive to manufacture and contain separable parts which may accidentally be swallowed and are difficult to use. In addition to the Rosenberg patent, self-ligating brackets having separable parts are disclosed in U.S. Pat. Nos. 4,371,337; 4,077,126; 4,419,178; 3,444,621; 4,268,249; 3,327,393; and 4,355,975.

Although the self-ligating orthodontic brackets disclosed in the Wallshein patents 3,052,028 and 3,724,074 do have a unitary construction, the configuration of the orthodontic brackets has been found to be inappropriate for the firm and proper retention of the arch wire in the base portion of the bracket.

An objective of the present invention is to provide a one-piece self-ligating slotted orthodontic bracket which has a low profile for comfort, and which is constructed to have a cover which exerts a continual force on the arch wire that may not fit all the way into the slot, so that over time the cover will slowly force the arch wire firmly and positively into the slot to be firmly retained on the bracket. The bracket may be easily applied either to the lingual or labial surface of a tooth. Moreover, the orthodontic bracket of the present invention is conceived to be easily constructed. In its very simplest and basic design, it may be compared to the action of the one-piece clothespin that is spread to hold the clothesline firmly in its grip.

SUMMARY OF THE INVENTION

A low profile self-ligating orthodontic bracket which may be adhesively attached to the lingual or labial surface of the tooth, which has a low profile, and which includes a transverse slot for receiving the arch wire. The self-ligating orthodontic bracket of the invention is constructed to include an integral resilient cover plate which extends over the slot and which is angularly self-biased against the base. The cover plate may be turned outwardly by the orthodontist to permit the arch wire to be inserted into the slot, and then released to turn against the base and trap the arch wire in the slot. The cover plate, when released, exerts a continuous pressure on the arch wire, pressing it into the depth of the slot to a position where it can best move the tooth into its desired position. The active functional aspect of the bracket will allow a larger wire to be placed partially in the slot and the action of the outer cover plate of this bracket will constantly force the arch wire into the slot, without the patient having to come in for many arch wire changes from very light wires to more heavy. By starting out with larger sized arch wires, the orthodontic bracket of the invention reduces the number of arch wire changes which necessitate patient visits.

DETAILED DESCRIPTION OF THE ILLUSTRATED EMBODIMENTS

The bracket of the present invention, as shown in FIGS. 1–4, is designated generally as 10. Bracket 10 has a base 10a and a cover plate 10b, as well as an adhesively backed base plate 10c which is integral with base 10a, or otherwise attached thereto. The base plate 10c is adhesively bonded to the labial or lingual surface of a tooth designated 12, this being achieved by any known bonding technique. Cover plate 10b is formed integral with base 10a, and is joined to the base along its lower edge 22. The cover plate 10b extends over a transverse slot 14 in base 10a. A typical arch wire 16 is supported in slot 14. A vertical passage 17 extends through base 10a perpendicular to the slot 14 in position to receive a hook to which an elastic may be attached, in accordance with known practice. Likewise, an external slot 20 extends transversely across the exterior of cover plate 10b parallel to slot 14 in a position to receive a ligature, if needed. Wings 18 are provided integral to base plate 10c on each side of the bracket, and these wings may be adjusted to assist in tooth rotation, in accordance with usual practice. Wings 18 could be part of the cover plate, if so desired, for the same rotation control. A recess 19 may also be provided in base 10a for receiving the ligature positioned in slot 20. Cover 10b has an inclined bite plane 21 which is inclined to the lower portion of the cover, and which may be used to occlude against the lower incisors in lingual orthodontic application, as disclosed in patent 4,337,037 which issued in the name of the present inventor. The bite plane 21 designates the upper portion of the cover 10b from the incisal edge of the cover plate, approximately one-third of the way from the incisal edge to the gingival edge, and this plane is approximately 45 degrees to the remainder of the surface of the cover 10b. This configuration is used in the lingual application of the bracket to prevent shearing of the bracket under occlusion forces and in the labial appliance to help shed food.

Figure 1:
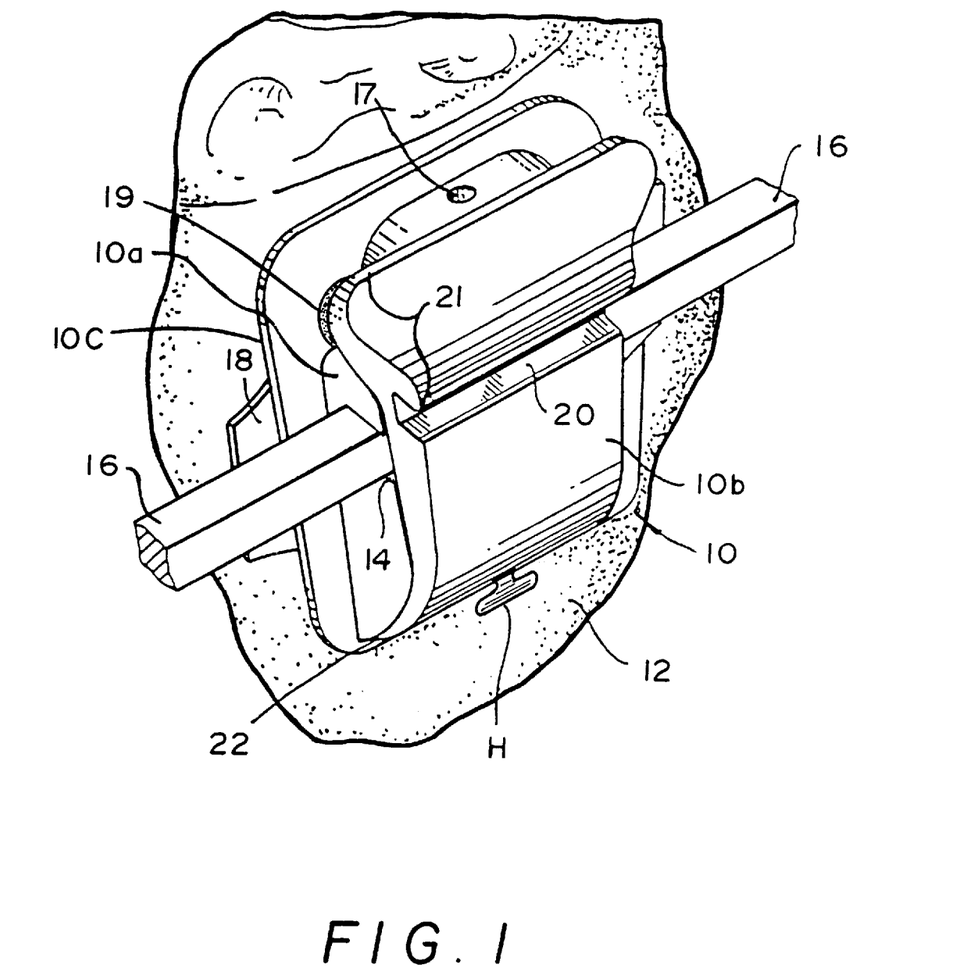
FIG. 1 is a perspective view of the orthodontic bracket constructed in accordance with one embodiment of the invention.
Figure 2:
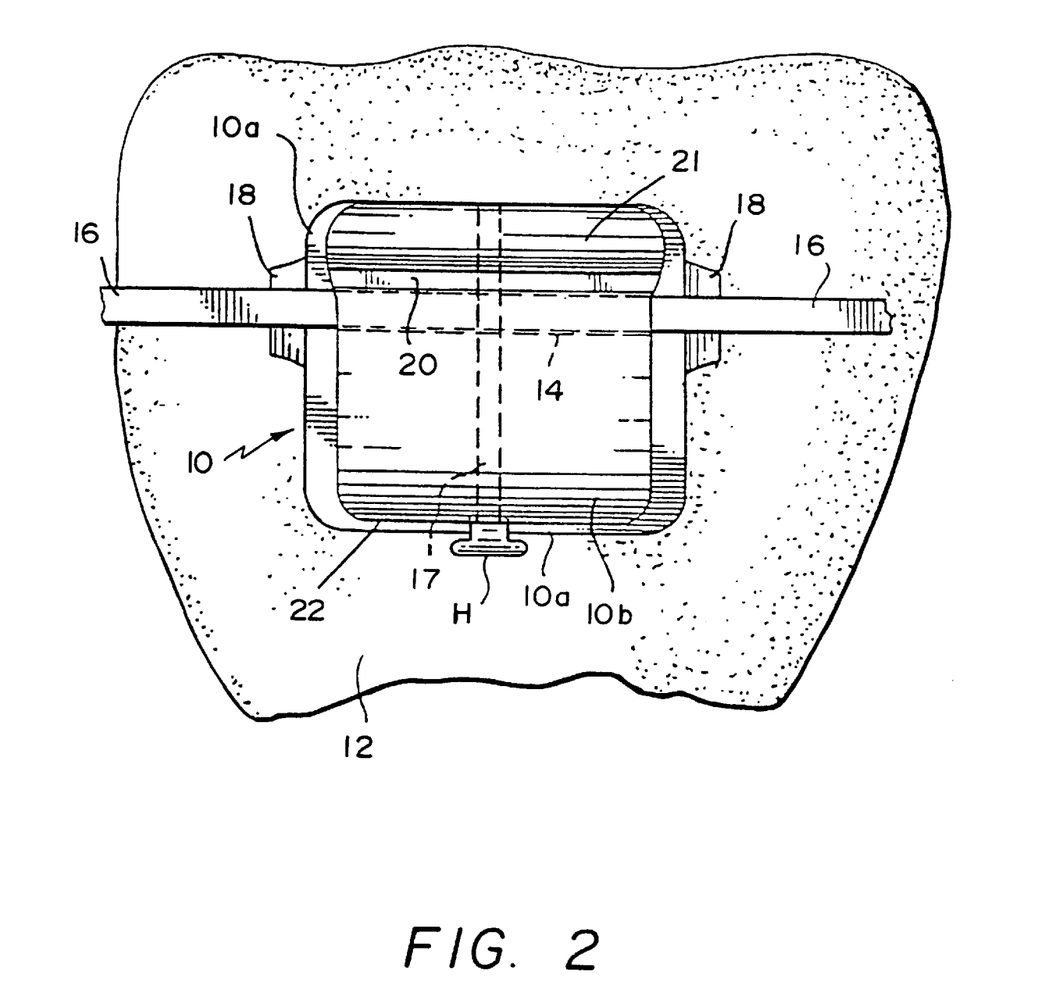
FIG. 2 is a front view of the bracket of FIG. 1.
Figure 3:
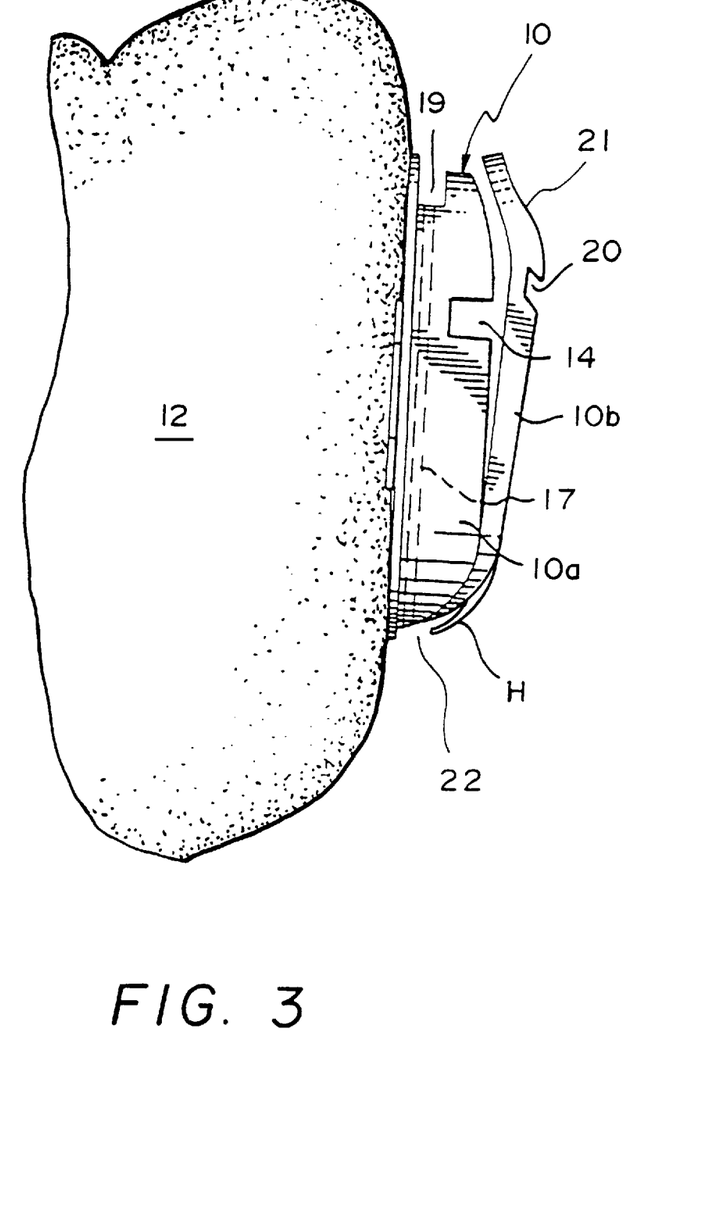
FIG. 3 is a side view of the bracket of FIG. 1 in an open position.
Figure 4:
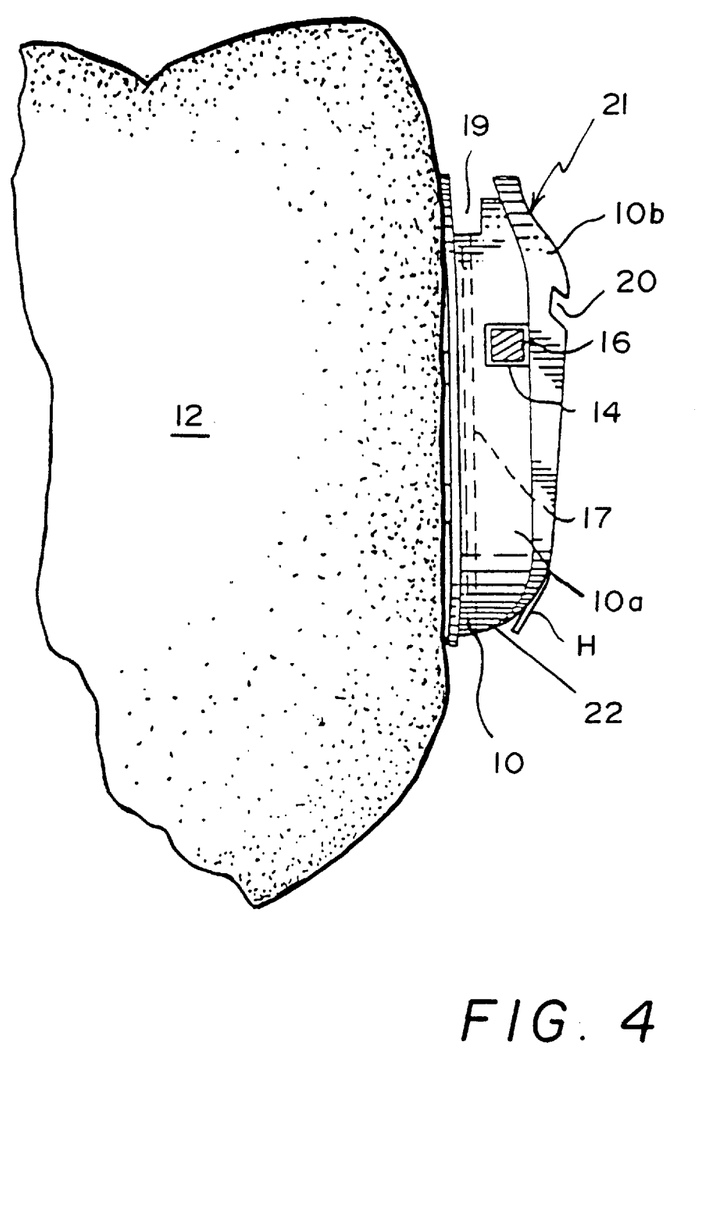
FIG. 4 is a side view, like FIG. 3, but with the bracket in a closed position.

The cover plate 10b is resiliently biased against the surface of base 10a, normally to trap the arch wire 16 within the slot 14, as best shown in FIG. 4. When it is desired either to insert the arch wire into the slot or to remove the arch wire from the slot, the orthodontist forces the cover plate 10b angularly away from the surface of base 10a, as shown in FIG. 3, so that the arch wire may be either removed from slot 14 or inserted into the slot. When the orthodontist releases the cover plate 10b, it moves angularly from the position shown in FIG. 3 to the position shown in FIG. 4 in order to trap the arch wire 16 within the slot 14. If necessary, a ligature may be inserted into slot 20 to reinforce the closure force of the cover plate 10b. A hook H is attached to the cover plate for assisting in opening the cover plate to allow access to slot 14.

Base 10a and cover plate 10b of bracket 10 may conveniently be formed of stainless steel, or other appropriate material. The cover plate may be tooth colored for aesthetic reasons for labial applications, and for that purpose may be formed either of solid plastic, porcelain or metal with tooth colored facing. Accordingly, the cover plate 10b forms an exterior resilient section for bracket 10, which may be opened to allow the arch wire 16 to be inserted into slot 14. The base 10a is the main body of the bracket and, as mentioned above, the arch wire slot 14 is cut into the base.

Figure 5:
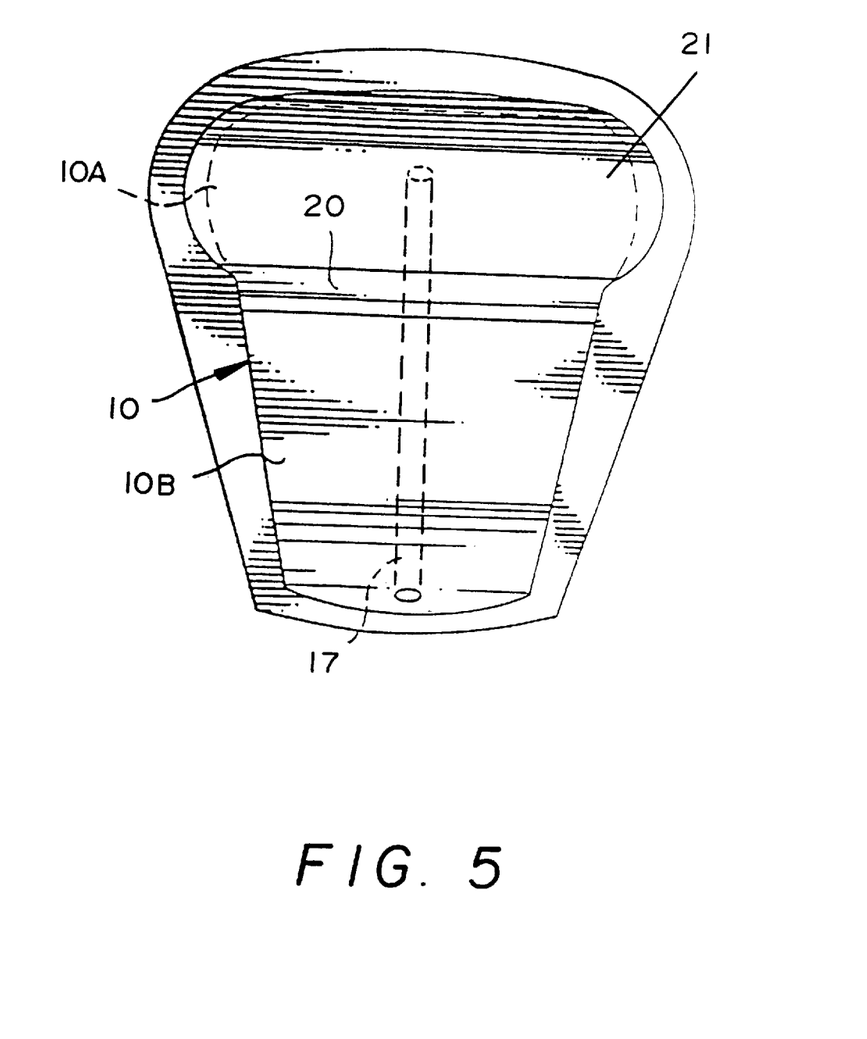
FIG. 5 is a front view of a slightly modified bracket.
Figure 6:
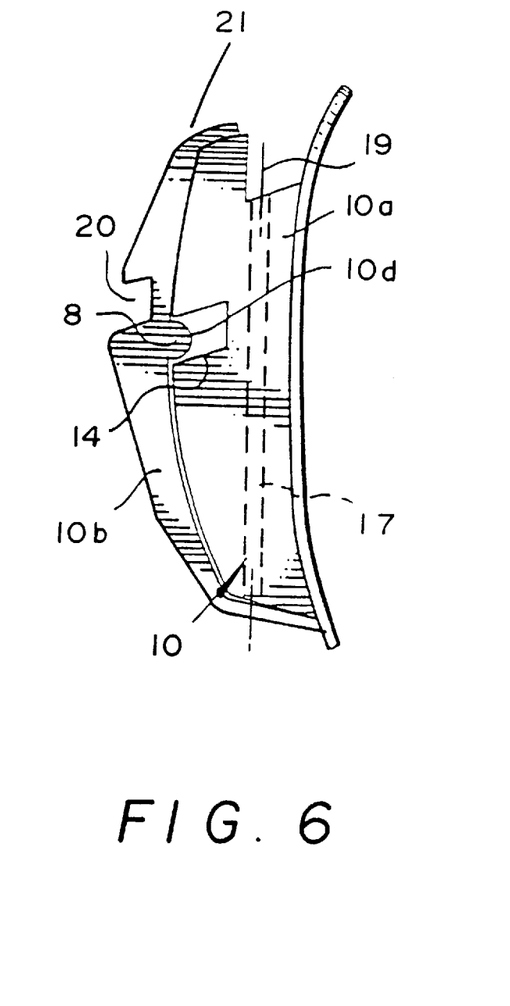
FIG. 6 is a side view of the bracket of FIG. 5.

In the embodiment of FIGS. 5 and 6, the cover plate 10b is configured so that its incisal edge extends around the top of the base 10a to prevent food from entering between the cover plate and the base and into slot 14. Also, cover plate 10b is equipped with a protuberance 10d (FIG. 6) which extends into slot 14 to serve as a pressure point to assure that the arch wire will be firmly held in the slot, especially when the arch wire is undersized.

Figure 7:
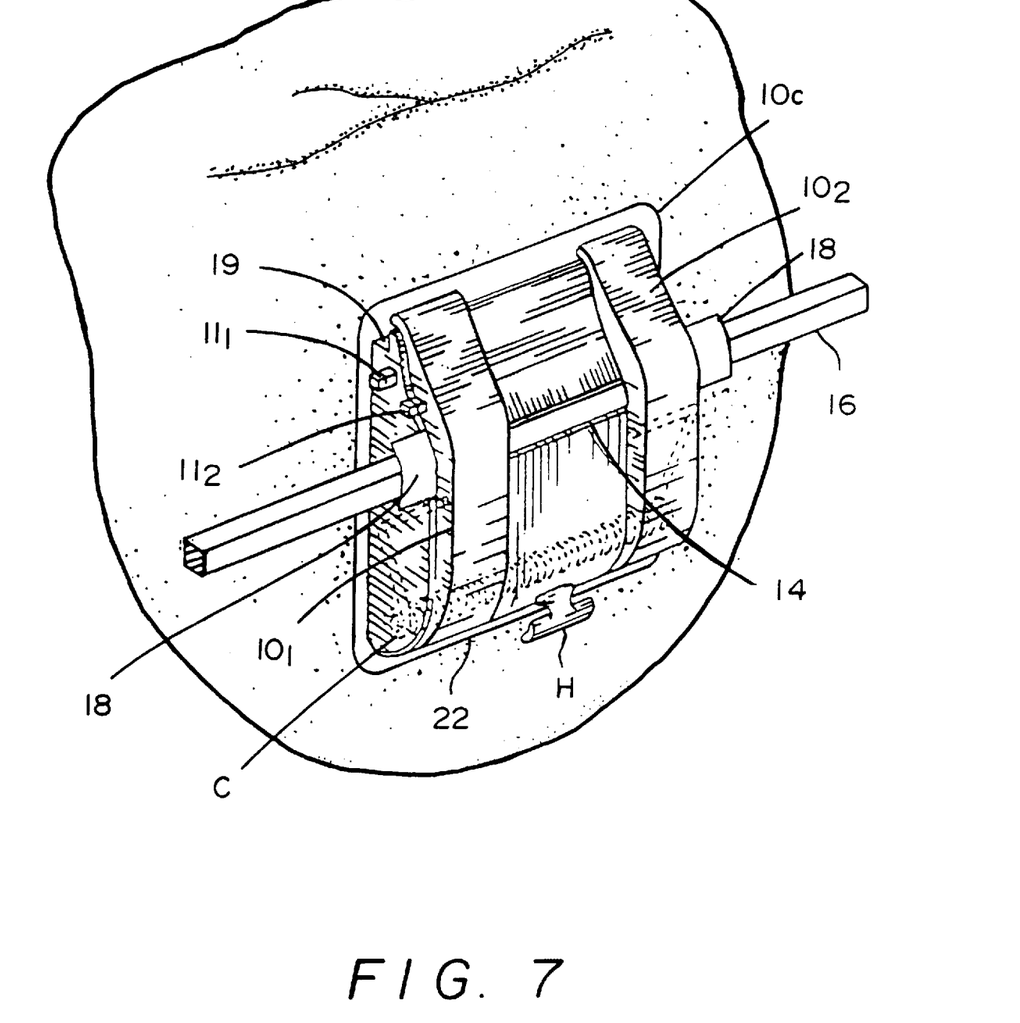
FIG. 7 is a perspective view of a modified form of the bracket having a cover plate formed as two separate arms and including a cover-retaining spring.

FIG. 7 shows a modified version of the bracket in which the cover plate is replaced by two separate arms $10_1$ and $10_2$ which are spaced apart and are joined by a strip 22 attached to the lower ends of the arms. The embodiment of FIG. 7 has increased resiliency as compared with the cover of the previous embodiments. Two labial hooks $11_1$ and $11_2$ are provided to assist closure, if necessary. Hook $11_1$ is part of the base 10a and hook $11_2$ is part of arm $10_1$ of the cover.

Accordingly, the cover plate is split into the two spaced arms $10_1$ and $10_2$ which are coupled to a coil spring C. The coil spring C provides additional pressure for closing the arms $10_1$ and $10_2$ against the arch wire 16, progressively working the arch wire into the slot 14. The coil spring C forces the arms $10_1$ and $10_2$ angularly toward the base plate 10a. The two hooks $11_1$ and $11_2$ are used as elastic attachments to assist the coil spring C in pressing the arch wire progressively into slot 14. In the embodiment of FIG. 7, the wings 18 are attached to the cover plate arms $10_1$, $10_2$ instead of to the base 10a, and assist in pressing the arch wire 16 into slot 14.

Figure 8:
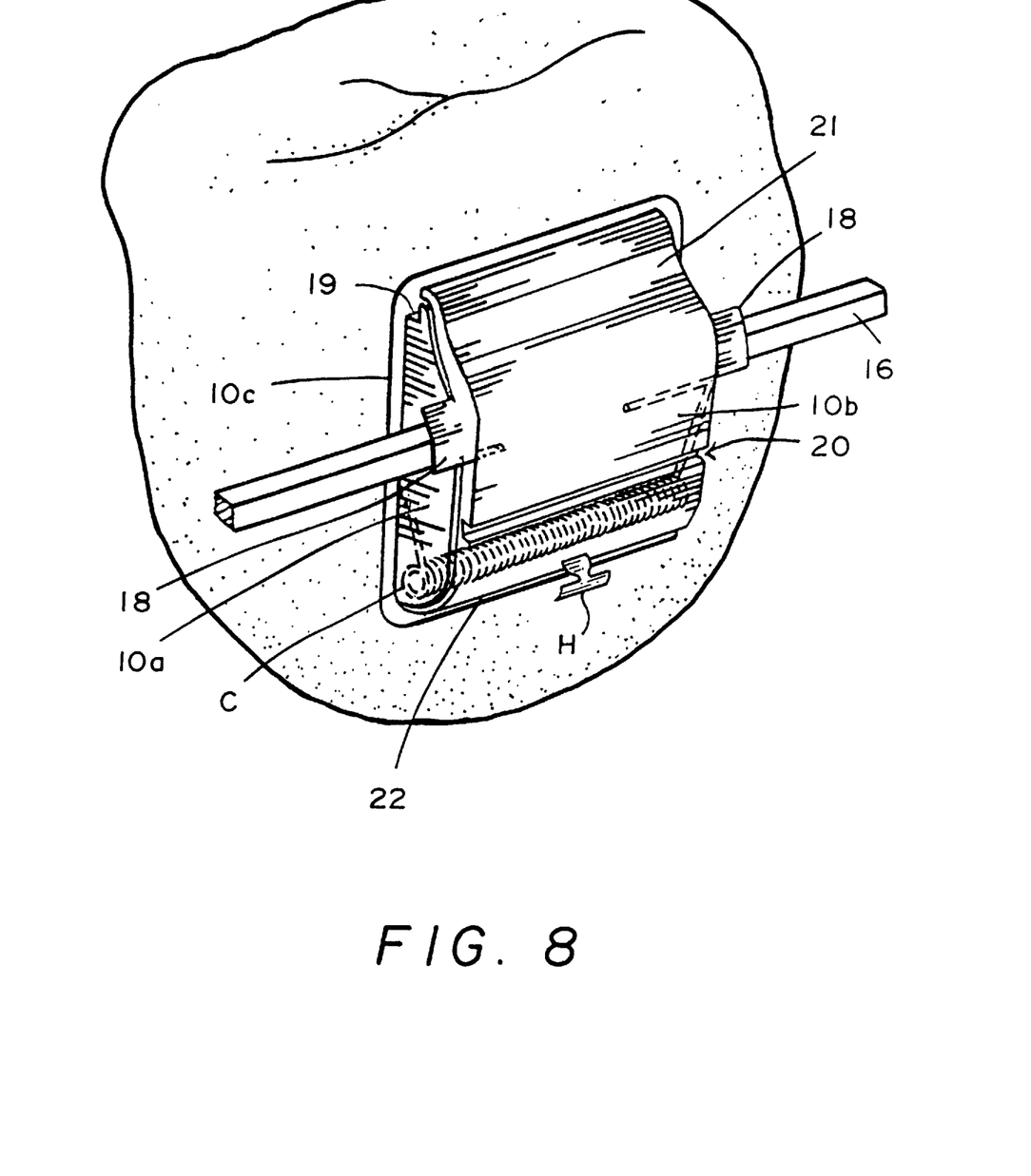
FIG. 8 is a perspective view of a further modified bracket having a one-piece cover plate and having a transverse slot for receiving a ligature to enhance the closure of the cover plate.

In the embodiment of FIG. 8, the cover plate 10b is of one piece, and the wings 18 are integral with the cover plate. In the embodiment of FIG. 8, a slot 20 replaces the labial protuberances $11_1$ and $11_2$ of FIG. 7, as in FIG. 1, to enhance the closure of the cover plate with a ligature, if necessary. The hook H is attached to the cover plate 10b, and it may be used for ligation or assistance in opening the cover plate 10b from the base plate 10a. The embodiment of FIG. 8 includes the coil spring C which is coupled to the base 10a and to cover 10b and assists in angularly exerting pressure on the cover plate 10b to force it against the base plate 10a.

Figure 9A:
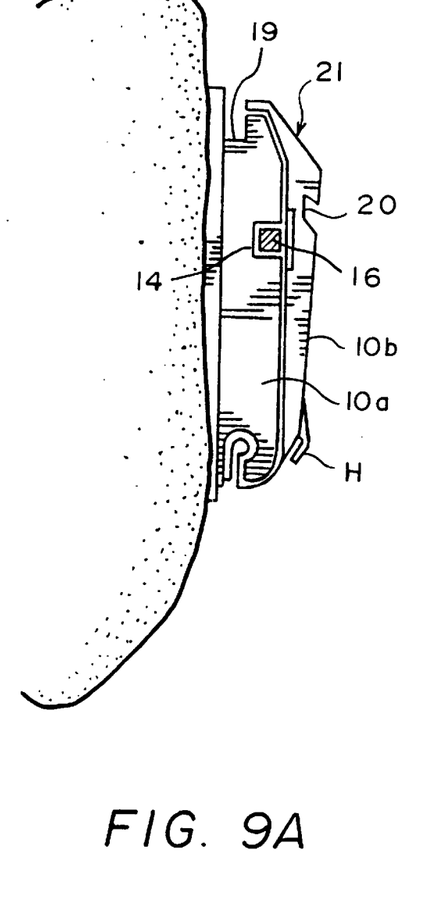
FIG. 9A is a side view of a bracket similar to the bracket of FIG. 8 but including a coil-type cover retaining spring of a different configuration from FIG. 8.
Figure 9B:
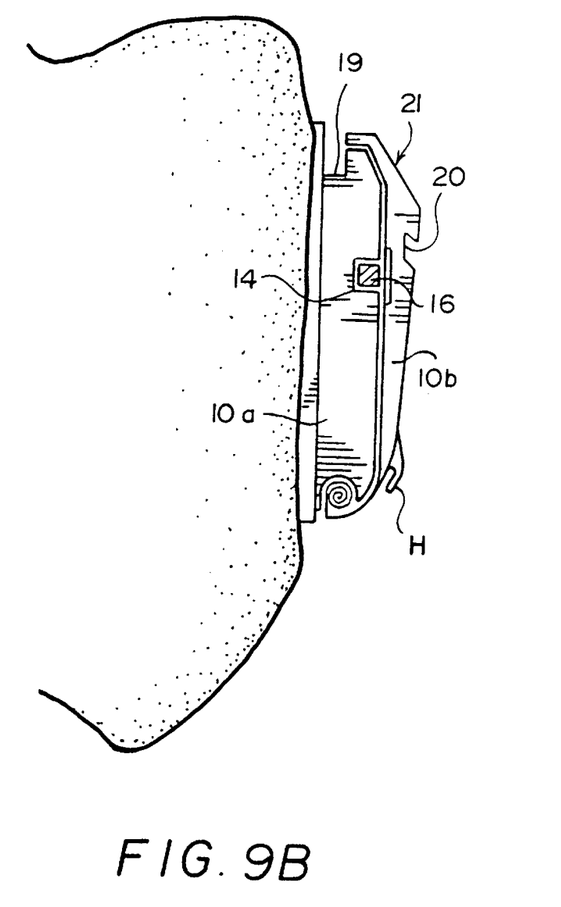
FIG. 9B is a side view of a bracket similar to the bracket of FIG. 9A but including a cover-retaining spring of a different configuration.

The embodiments of FIGS. 9A and 9B are similar to the previous embodiments, but use different types of coil springs $C_1$ and $C_2$.

Figure 10A:
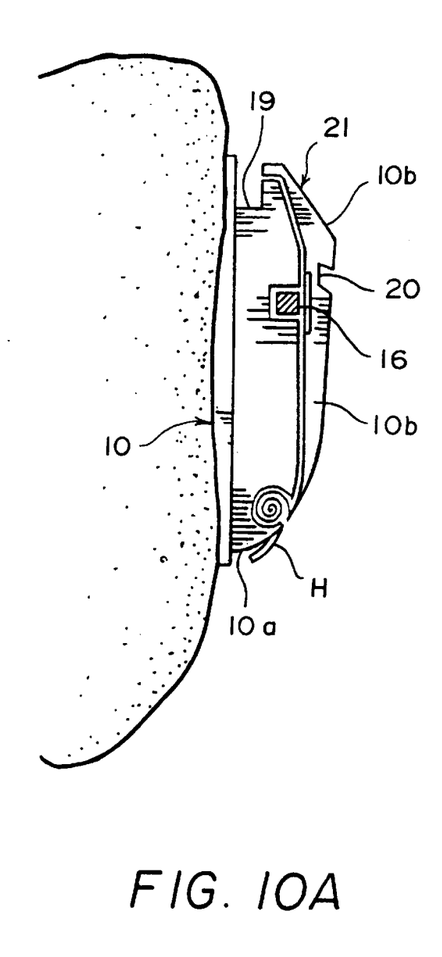
FIGS. 10A and 10B are side views of a bracket similar to the bracket of FIG. 8 but with hooks mounted on the base, rather than on the cover as is the case with the brackets of FIGS. 9A and 9B.
Figure 10B:
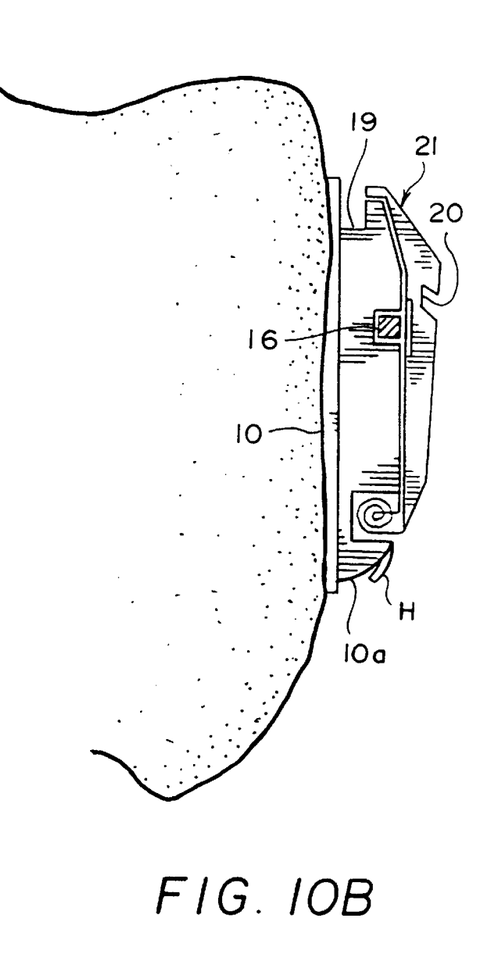

In the embodiment of FIG. 10A, hook H is attached to the base 10a rather to the cover 10b, and is used for ligation purposes only. This also applies to the embodiment shown in FIG. 10B.

Figure 11A:
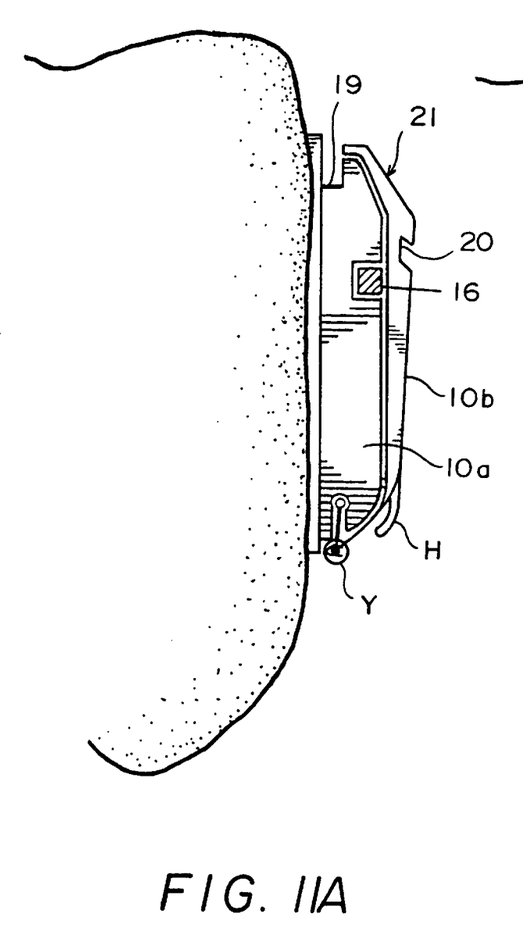
FIGS. 11A and 11B show further modifications of the bracket.

In the embodiment of FIG. 11A, the hook is attached to the cover for ligation purposes and also to assist in the opening of the cover 10b.

Figure 11B:
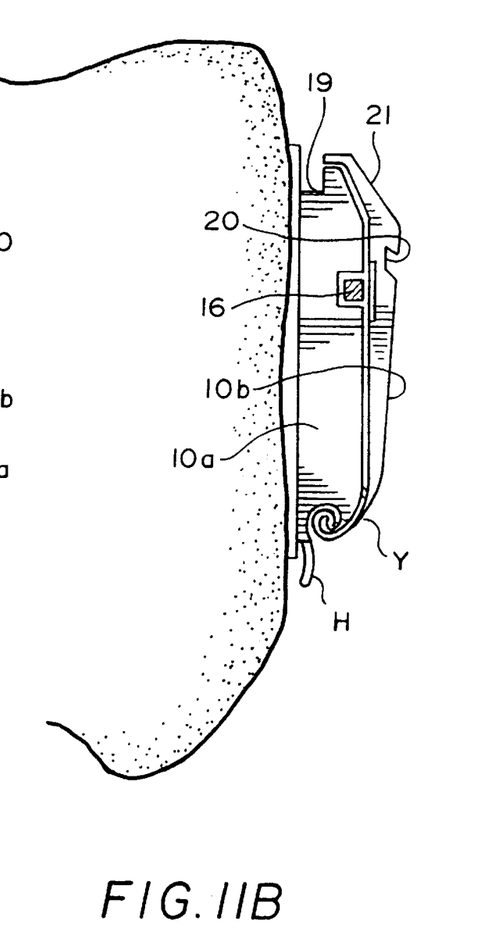

In the embodiment of FIG. 11A, the cover plate 10b is hinged to the base 10a by a hinge Y, and a different type of hinge $Y_1$ is used in the embodiment 11B.

Figure 12:
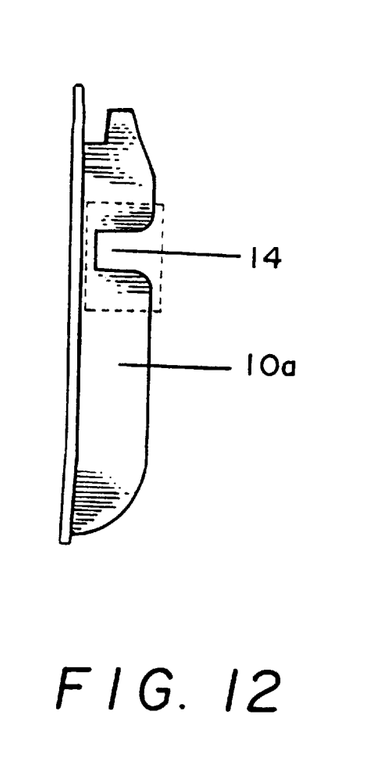
FIG. 12 is a side view of an embodiment similar to the embodiment of FIG. 1 having a transverse slot having a flared opening.

FIG. 12 shows how the outer edge of the slot 14 in bracket may be flared to facilitate the entrance of the arch wire into the slot.

Figure 13:
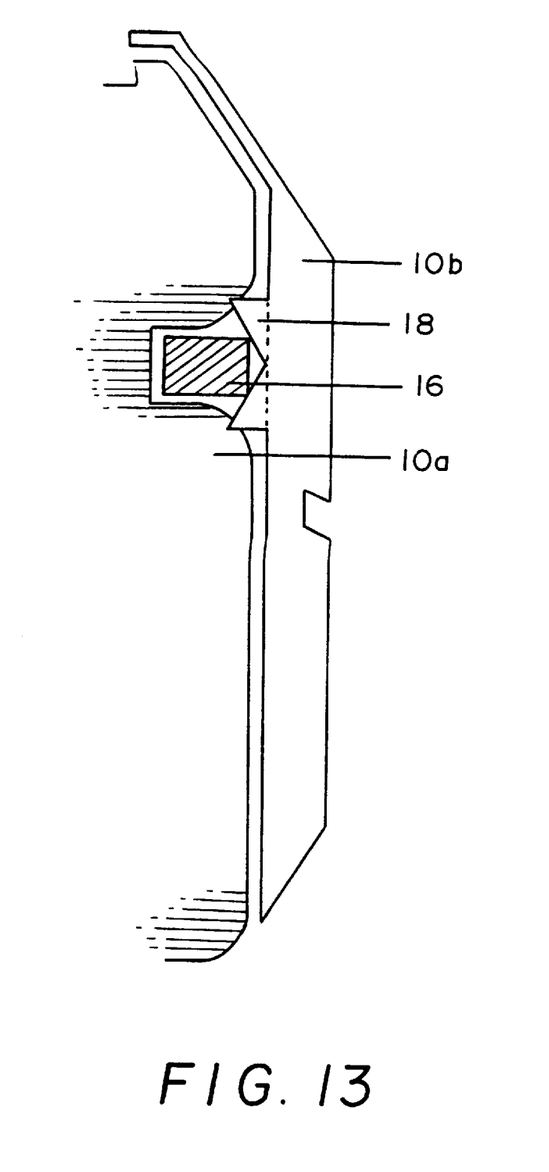
FIG. 13 is a side view of an embodiment like FIG. 7 having wings with a particular configuration.

FIG. 13 shows a side view of the cover plate 10b and the internal V-shape of a modified wing 18 acting to minimize friction and maximize rotation control and arch wire flexibility.

The invention provides, therefore, a self-ligating orthodontic bracket of a simple nonbreakable design, which has a one-piece construction to eliminate complication of manufacturing and use. The resilient pressure of the cover plate 10b against the base 10a provides a continual pressure for maximal tooth control by the arch wire 16. The bracket has a low profile to provide for maximum comfort to the patient and a minimum of speech impediment. The overall height of the bracket is made small for maximum patient comfort.

The brackets of the invention have a feature in that they may be placed close to the gingiva. This can be an advantage in terms of occlusal interferences. The brackets of the invention are relatively small and, consequently, if used on the lingual side of the tooth they do not interfere with the gingival tissue or the tongue. However, if so desired, the brackets may be used on the labial side as in conventional orthodontic therapy. Moreover, as pointed out, the brackets may also be applied to the lingual surface of the tooth to act as a fixed lingual appliance.

It will be appreciated that while particular embodiments of the invention have been shown and described, modifications may be made. It is intended in the claims to cover all modifications which come within the true spirit and scope of the invention.

I claim:

1. A self-ligating orthodontic bracket comprising a base plate having a rear surface and a front surface, adhesive means mounted on said rear surface of said base plate to attach the bracket to the surface of a tooth, and said base plate having its front surface provided with a transverse slot for receiving an arch wire in partially engaged position displaced up from the bottom of the slot, and a cover plate extending across the front surface of said base plate to cover said base plate and said slot, said cover plate having a lower edge connected to said base plate to cause said cover plate to be resiliently self-biased against the front surface of said base plate for continually and progressively forcing the arch wire down into the transverse slot while the bracket is in place, the cover plate being separated into two sections, a first lateral protuberance mounted on one of the sections of the cover plate, and a second lateral protuberance mounted on the base plate, said first and second protuberances being used for elastic attachment to enhance cover plate pressure toward the base plate.

2. The orthodontic bracket defined in claim 1, in which said transverse slot of the base plate has a flared configuration at its entrance to facilitate the entrance of the arch wire into it.

3. The orthodontic bracket defined in claim 1, in which said base plate and said cover plate are joined at said lower edge of said cover plate and are formed of a resilient material.

4. The orthodontic bracket defined in claim 1, in which the rear surface of said base plate is adapted to be adhesively attached to the lingual or labial surface of the tooth.

5. The orthodontic bracket defined in claim 1, and which includes a pair of lateral wings mounted on the cover plate to assist pressing the arch wire into the arch wire slot.

6. The orthodontic bracket defined in claim 1, and which includes an integral coil spring connecting the lower edge of the cover plate to the base plate.

7. The orthodontic bracket defined in claim 1, and which is shaped to have a low profile for maximizing comfort when the bracket is attached to a tooth.

8. The orthodontic bracket defined in claim 1, and which has a built-in inclined plane for occlusion forces and shedding of masticated food.

9. The orthodontic bracket defined in claim 1, and which includes hooks for elastic or ligature attachment mounted on the cover plate or base plate.

* * * * *